(12) United States Patent
Miracle

(10) Patent No.: US 7,030,075 B2
(45) Date of Patent: Apr. 18, 2006

(54) ORGANIC ACTIVATOR

(75) Inventor: Greogory Scot Miracle, Hamilton, OH (US)

(73) Assignee: Procter & Gamble Company, Cincinnati, OH (US)

(*) Notice: Subject to any disclaimer, the term of this patent is extended or adjusted under 35 U.S.C. 154(b) by 240 days.

(21) Appl. No.: 10/737,427

(22) Filed: Dec. 16, 2003

(65) Prior Publication Data

US 2004/0142844 A1    Jul. 22, 2004

Related U.S. Application Data

(60) Provisional application No. 60/434,619, filed on Dec. 18, 2002.

(51) Int. Cl.
  *C11D 3/26* (2006.01)
  *C11D 3/28* (2006.01)
  *C11D 3/395* (2006.01)

(52) U.S. Cl. ............ 510/314; 510/320; 510/322; 510/340; 510/372; 510/376; 510/500; 510/504; 548/566

(58) Field of Classification Search ........ 510/314, 510/320, 322, 340, 372, 376, 500, 504; 8/111, 8/137; 548/566; 252/186.38, 186.39
See application file for complete search history.

(56) References Cited

U.S. PATENT DOCUMENTS

| | | | |
|---|---|---|---|
| 3,281,452 A | 10/1966 | Kapar et al. | |
| 4,430,243 A | 2/1984 | Bragg | |
| 5,486,303 A | 1/1996 | Capeci | |
| 5,489,392 A | 2/1996 | Capeci | |
| 5,516,448 A | 5/1996 | Capeci | |
| 5,565,422 A | 10/1996 | Del Greco | |
| 5,569,645 A | 10/1996 | Dinniwell | |
| 5,574,005 A | 11/1996 | Welch | |
| 5,576,282 A | 11/1996 | Miracle | |
| 5,595,967 A | 1/1997 | Miracle | |
| 5,597,936 A | 1/1997 | Perkins | |
| 5,599,781 A | 2/1997 | Haeggberg | |
| 5,691,297 A | 11/1997 | Nassano | |
| 5,817,614 A | 10/1998 | Miracle | |
| 5,879,584 A | 3/1999 | Bianchetti | |
| 6,063,750 A | 5/2000 | Loffler et al. | |
| 6,211,130 B1 | 4/2001 | Josa Pons | |
| 6,221,824 B1 | 4/2001 | Lietzmann et al. | |
| 6,225,274 B1 | 5/2001 | Nitsch et al. | |
| 6,306,812 B1 | 10/2001 | Perkins | |
| 6,326,348 B1 | 12/2001 | Vinson | |
| 2002/0107163 A1* | 8/2002 | Borchers et al. ............ 510/302 |

FOREIGN PATENT DOCUMENTS

| | | |
|---|---|---|
| CA | 2298847 | 5/2000 |
| CA | 2299437 | 8/2000 |
| CA | 2303638 A1 | 9/2000 |
| DE | 19629159 A1 | 1/1998 |
| EP | 0 303 520 A2 | 2/1989 |
| EP | 0 464 880 A1 | 1/1992 |
| EP | 0 790 244 A1 | 8/1997 |
| WO | WO 99/014296 A1 | 3/1999 |
| WO | WO 99/63038 A1 | 12/1999 |
| WO | WO 02/12175 A2 | 2/2002 |
| WO | WO 02/12425 A1 | 2/2002 |
| WO | WO 02/012426 A1 | 2/2002 |

OTHER PUBLICATIONS

Chiba, et al., "Anodic Cyanation of Tertiary Aliphatic and Heterocyclic Amines", J. Org. Chem. 1977, vol. 42, No. 18, pp. 2973-2977.

Luten, "The Preparation of Aminonitriles and Their Quaternary Ammonium Derivatives", D B., J. Org, Chem. 1939, vol. 3, No. 6, pp. 588-597.

XP002278511 SU 1 809 602 A (Vsesoyuznyj) Jun. 30, 1994 (Abstract).

* cited by examiner

*Primary Examiner*—Gregory R. Del Cotto
(74) *Attorney, Agent, or Firm*—James F. McBride; Kim W. Zerby; Steve W. Miller

(57) ABSTRACT

This invention relates to organic activators having the following formula:

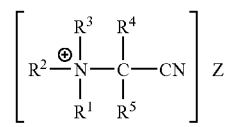

wherein Z is a charge equalizing ion and one or more of the moieties $R^1$, $R^2$, $R^3$, $R^4$ and $R^5$ are modified such that the one or more of the drawbacks associated with this class of molecule are essentially eliminated, cleaning compositions comprising such activators; and processes for making and using such activators and cleaning products.

7 Claims, No Drawings

ORGANIC ACTIVATOR

CROSS-REFERENCES TO RELATED APPLICATIONS

This application claims priority under 35 U.S.C. § 119(e) to U.S. Provisional Application Ser. No. 60/434,619 filed Dec. 18, 2002.

FIELD OF INVENTION

This invention relates to organic activators and cleaning compositions comprising such activators, and processes for making and using such activators and cleaning products.

BACKGROUND OF THE INVENTION

Oxygen bleaching agents, for example hydrogen peroxide, are typically used to facilitate the removal of stains and soils from clothing and various surfaces. Unfortunately such agents are extremely temperature rate dependent. As a result, when such agents are employed in colder solutions, the bleaching action of such solutions is markedly decreased.

In an effort to resolve the aforementioned performance problem, the industry developed a class of materials known as "bleach activators". However, as such materials rapidly lose their effectiveness at solution temperatures of less than 40° C., new organic activators such as 1-cyano-N,N,N-trimethylmethanaminium chloride were developed. In general, while such activators may be effective in lower temperature water conditions, they impart offensive odors to wash liquors, and are hygroscopic, which results in product instability, handling drawbacks and efficiency drawbacks. Accordingly, there is a need for an improved organic activator.

SUMMARY OF THE INVENTION

The present invention relates to organic activators having the following general formula:

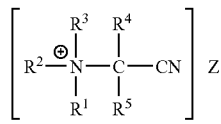

wherein Z, when required, is a charge equalizing ion and one or more of the moieties $R^1$, $R^2$, $R^3$, $R^4$ and $R^5$ are modified such that one or more of the drawbacks associated with this class of molecule are essentially eliminated.

The present invention also relates to cleaning compositions comprising said organic activators, and processes for making and using the aforementioned organic activators and cleaning compositions.

All documents cited are, in relevant part, incorporated herein by reference; the citation of any document is not to be construed as an admission that it is prior art with respect to the present invention.

DETAILED DESCRIPTION OF THE INVENTION

Definitions

As used herein, the term "cleaning composition" includes, unless otherwise indicated, granular or powder-form all-purpose or "heavy-duty" washing agents, especially laundry detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, laundry bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the phrase "is independently selected from the group consisting of . . . " means that moieties or elements that are selected from the referenced Markush group can be the same, can be different or any mixture of elements as indicated in the following example:

A molecule having 3 R groups wherein each R group is independently selected from the group consisting of A, B and C.

Here the three R groups may be: AAA, BBB, CCC, AAB, AAC, BBA, BBC, CCA, CCB, ABC. As used herein, "substituted" means that the organic composition or radical to which the term is applied is:

(a) made unsaturated by the elimination of elements or radical; or (b) at least one hydrogen in the compound or radical is replaced with a moiety containing one or more (i) carbon, (ii) oxygen, (iii) sulfur, (iv) nitrogen or (v) halogen atoms; or (c) both (a) and (b).

Moieties which may replace hydrogen as described in (b) immediately above, that contain only carbon and hydrogen atoms are hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Moieties containing oxygen atoms that may replace hydrogen as described in (b) immediately above include, but are not limited to, hydroxy, acyl or keto, ether, epoxy, carboxy, and ester containing groups. Moieties containing sulfur atoms that may replace hydrogen as described in (b) immediately above include, but are not limited to, the sulfur-containing acids and acid ester groups, thioether groups, mercapto groups and thioketo groups. Moieties containing nitrogen atoms that may replace hydrogen as described in (b) immediately above include, but are not limited to, amino groups, the nitro group, azo groups, ammonium groups, amide groups, azido groups, isocyanate groups, cyano groups and nitrile groups. Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety.

It is understood that any of the above moieties (b)(i) through (b)(v) can be substituted into each other in either a monovalent substitution or by loss of hydrogen in a polyvalent substitution to form another monovalent moiety that can replace hydrogen in the organic compound or radical.

Organic Activator

Bleach activators such as 1-cyano-N,N,N-trimethylmethanaminium chloride impart offensive odors to wash liquors, and are hygroscopic which results in product instability, handling drawbacks and efficiency drawbacks. While not being bound by theory, Applicants believe that such malodor may arise as a result of the release of an amine compound due to hydroperoxyl anion induced cleavage of the single bond between the quaternary nitrogen and the carbon atom attached to the nitrile (CN) group. In addition to demonstrating improved stability, handling and efficiency characteristics, embodiments of the instant invention address the malodor issue as they do not release appreciable amounts of odiferous amine compounds.

In one aspect of Applicants' invention, Applicants' activator has the general formula:

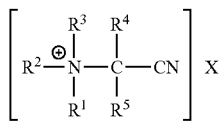

wherein
a.) $R^4$ and $R^5$ are independently hydrogen, or substituted or unsubstituted alkyl, alkenyl or aryl groups containing from 1 to 18 carbon atoms;
b.) at least one of $R^1$, $R^2$ or $R^3$ is a hydroxyalkyl moiety comprising at least 2 carbon atoms;
c.) any remaining $R^1$, $R^2$ or $R^3$ moieties are independently substituted or unsubstituted alkyl, alkenyl or aryl groups containing from 1 to 18 carbon atoms; and
d.) X, when present, is a charge-equalizing anion. Suitable anions include, but are not limited to, chloride, bromide, sulfate, methyl sulfate, dodecyl sulfate, sulfonate, p-toluenesulfonate, fluorosulfate, trifluoromethylsulfate, acetate, and decanoate.

Certain embodiments of the aforementioned compound have all of the $R^1$, $R^2$ or $R^3$ moieties' hydroxyl groups separated from said compound's quaternary nitrogen by at least 2 carbon atoms. Certain embodiments of the aforementioned compound have all of the $R^1$, $R^2$ or $R^3$ moieties' hydroxyl groups separated from said compound's quaternary nitrogen by at least 3 carbon atoms. In certain embodiments of the aforementioned compound, at least one of $R^1$, $R^2$ or $R^3$ is a linear hydroxyalkyl moiety comprising from 2 to 12 carbons. In other embodiments of the aforementioned compound, at least one of $R^1$, $R^2$ or $R^3$ is a linear hydroxyalkyl moiety comprising from 3 to 12 carbons and all of said linear hydroxyalkyl moieties' hydroxyl groups are separated from said compound's quaternary nitrogen by at least 2 carbon atoms.

In another aspect of Applicants' invention, Applicants' activator has the general formula:

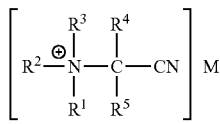

wherein
a.) $R^4$ and $R^5$ are independently hydrogen, or substituted or unsubstituted alkyl, alkenyl or aryl groups containing from 1 to 18 carbon atoms;
b.) at least one of $R^1$, $R^2$ or $R^3$ is a moiety selected from the group consisting of $R^6OSO_2^-$, $R^6OSO_3^-$, $R^6OPO_2^-$, $R^6OCO_2^-$, $R^6SO_2^-$, $R^6SO_3^-$, and $R^6CO_2^-$; wherein $R^6$ is independently a $C_1$ to $C_{20}$ substituted or unsubstituted alkyl; provided that when one or more of $R^1$, $R^2$ or $R^3$ is $R^6CO_2^-$; the $CO_2^-$ group of any $R^6CO_2^-$ moiety is separated from said compound's quaternary nitrogen by at least 2 carbon atoms; and
c.) any remaining $R^1$, $R^2$ or $R^3$ moieties are independently substituted or unsubstituted alkyl, alkenyl or aryl groups containing from 1 to 18 carbon atoms.
d.) M, when present, is a charge balancing cation. Suitable cations include, but are not limited to, Group IA and Group IIA elements such as lithium, sodium, potassium, magnesium and calcium.

In certain embodiments of the aforementioned activator, only one of $R^1$, $R^2$ or $R^3$ is a moiety selected from the group consisting of $R^6OSO_2^-$, $R^6OSO_3^-$, $R^6OPO_2^-$, $R^6OCO_2^-$, $R^6SO_2^-$, $R^6SO_3^-$, and $R^6CO_2^-$.

In another aspect of Applicants' invention, Applicants' activator has the general formula:

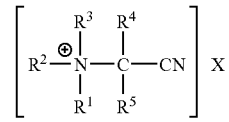

wherein
a.) $R^1$, $R^2$, and $R^3$, are independently selected from the group consisting of substituted or unsubstituted $C_1$ to $C_{20}$ alkyl moieties;
b.) $R^4$ and $R^5$ are independently selected from the group consisting of hydrogen, or substituted or unsubstituted $C_1$ to $C_{20}$ alkyl moieties, provided that $R^4$ and $R^5$ are not both hydrogen;
c.) at least one of $R^1$, $R^2$ or $R^3$ is joined with at least one of $R^4$ and $R^5$ to form a ring comprising at least 5 atoms, one of said atoms being the quaternary nitrogen of said compound; and
d.) X, when present, is a charge-equalizing anion. Suitable anions include, but are not limited to, chloride, bromide, sulfate, methyl sulfate, dodecyl sulfate, sulfonate, p-toluenesulfonate, fluorosulfate, trifluoromethylsulfate, acetate, and decanoate.

In certain embodiments of the aforementioned activator, only one of $R^1$, $R^2$, or $R^3$ is joined with only one of $R^4$ or $R^5$ to form a ring comprising at least 5 atoms, one of said atoms being the quaternary nitrogen of said compound.

Processes of Making Organic Activators

Suitable routes for preparing Applicants' organic activators include, but are not limited to, a process of making a bleach activator having the formula:

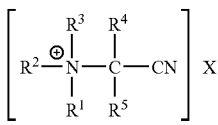

wherein $R^4$ and $R^5$ are independently hydrogen, or substituted or unsubstituted alkyl, alkenyl or aryl groups containing from 1 to 18 carbon atoms; at least one of $R^1$, $R^2$ or $R^3$ is a hydroxyalkyl moiety comprising at least 2 carbon atoms; any remaining $R^1$, $R^2$ or $R^3$ moieties are independently substituted or unsubstituted alkyl, alkenyl or aryl groups containing from 1 to 18 carbon atoms; and X is a charge-equalizing anion said process comprising the steps of:
Reacting an amine having the formula

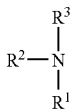

wherein $R^1$, $R^2$ and $R^3$ are as defined above, with an acetonitrile derivative having the formula:

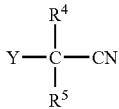

wherein $R^4$ and $R^5$ are as defined above and Y is moiety that upon displacement by the amine becomes X as defined above; or
reacting an amine having the formula:

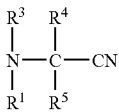

wherein $R^1$, $R^3$, $R^4$ and $R^5$ are as defined above, with a compound having the formula

wherein R is as defined above and Y is moiety that upon displacement by the amine becomes X as defined above.
A process of making a zwitterionic bleach activator said activator comprising only one anionic moiety and only one quaternary nitrogen, said activator having the formula:

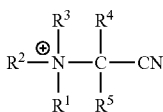

wherein $R^4$ and $R^5$ are independently hydrogen, or substituted or unsubstituted alkyl, alkenyl or aryl groups containing from 1 to 18 carbon atoms; only one of $R^1$, $R^2$ or $R^3$ is a moiety selected from the group consisting of $R^6OSO_2^-$, $R^6OSO_3^-$, $R^6OPO_2^-$, $R^6OCO_2^-$, $R^6SO_2^-$, $R^6SO_3^-$, and $R^6CO_2^-$;
wherein $R^6$ is independently a $C_1$ to $C_{20}$ substituted or unsubstituted alkyl; provided that when $R^1$, $R^2$ or $R^3$ is $R^6CO_2^-$; the $CO_2^-$ group of the $R^6CO_2^-$ moiety is separated from said compound's quaternary nitrogen by at least 2 carbon atoms; and the remaining $R^1$, $R^2$ or $R^3$ moieties are independently substituted or unsubstituted alkyl, alkenyl or aryl groups containing from 1 to 18 carbon atoms, said process comprising the steps of reacting an amine having the formula:

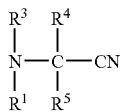

wherein $R^1$, $R^3$, $R^4$ and $R^5$ are as defined above, with a compound having the formula:

wherein $R^2$ is a moiety selected from the group consisting of $R^6OSO_2^-M$, $R^6OSO_3^-M$, $R^6OPO_2^-M$, $R^6OCO_2^-M$, $R^6SO_2^-M$, $R^6SO_3^-M$, and $R^6CO_2^-M$ wherein M is a charge neutralizing cation and Y is moiety that upon displacement by the amine becomes a charge neutralizing anion which when combined with M forms an acid or a salt; or

wherein $R^6$ is $C_1$ to $C_{20}$ substituted or unsubstituted alkylene and G is selected from the group consisting of $OSO_2$, $OSO_3$, $OPO_2$, $OCO_2$, $S(O)O$, $SO_3$ and $CO_2$.
A process of making a bleach activator having the formula:

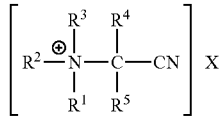

wherein $R^1$, $R^2$ and $R^3$ are independently selected from the group consisting of substituted or unsubstituted $C_1$ to $C_{20}$ alkyl moieties; $R^4$ and $R^5$ are independently selected from the group consisting of hydrogen, or substituted or unsubstituted $C_1$ to $C_{20}$ alkyl moieties, provided that $R^4$ and $R^5$ are not both hydrogen; at least one of $R^1$, $R^2$ or $R^3$ is joined with at least one of $R^4$ and $R^5$ to form a ring comprising at least 5 atoms, one of said atoms being the quaternary nitrogen of said compound; and X, when present, is a charge-equalizing anion, said process comprising the steps of reacting an amine having the formula:

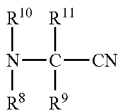

wherein $R^8$, $R^9$, $R^{10}$ and $R^{11}$ are independently selected from the group consisting of substituted or unsubstituted $C_1$ to $C_{20}$ alkyl moieties; and at least one of $R^8$ or $R^{10}$ is joined with at least one of $R^9$ or $R^{11}$ to form a ring comprising at least 5 atoms, one of said atoms being the nitrogen of said amine; with a compound selected from the group consisting of:

wherein $R^2$ is as defined above and Y is moiety that upon displacement by the amine becomes X as defined above; or

wherein $R^6$ is $C_1$ to $C_{20}$ substituted or unsubstituted alkylene and G is selected from the group consisting of $OSO_2$, $OSO_3$, $OPO_2$, $OCO_2$, $SO_2$, $SO_3$ and $CO_2$.

Suitable raw materials used in the aforementioned processes include amines such as 6-(dimethylamino)-1-hexanol; 3-(dimethylamino)-1-propanol; 2-(dimethylamino)-ethanol; dimethylaminoacetonitrile; 3-(dimethylamino)-1-propanesulfonic acid; 1-methyl-2-piperidinecarbonitrile; 1-methyl-2-pyrrolidinecarbonitrile; and 6-(dimethylamino) hexanoic acid; acetonitrile derivatives such as chloroacetonitrile; bromoacetonitrile; [[(4-methylphenyl)sulfonyl]oxy]acetonitrile; [(phenylsulfonyl)oxy]acetonitrile; [(methylsulfonyl)oxy]acetonitrile; trifluoromethane sulfonic acid, cyanomethyl ester; 1-octanesulfonic acid, cyanomethyl ester; and benzenemethanesulfonic acid, cyanomethyl ester; suitable compounds having the formula:

such as 2-chloroethanol; 3-chloro-1-propanol; 6-chloro-1-hexanol; 4-methylbenzenesulfonic acid 6-hydroxyhexyl ester; 6-chlorohexanoic acid; and methyl 4-methylbenzenesulfonate; and compounds having the formula:

such as 1,2-oxathiolane-2,2-dioxide; 1,2-oxathiane-2,2-dioxide; 1,3,2-dioxathiolane-2,2-dioxide; 4-octyl-1,3,2-dioxathiolane-2,2-dioxide; and 2-oxetanone.

The aforementioned processes may be conducted in any suitable organic solvent, including anhydrous polar, aprotic solvents such as diethyl ether, tetrahydrofuran, dioxane, and acetonitrile under conditions suitable to accomplish formation of the quaternary nitrogen. This may in some cases be accomplished with prolonged stirring at room temperature or may require heating at temperatures up to reflux, which will vary depending on the solvent or solvent system used. Commercial quantities of Applicants' organic activator can be produced using a variety of reaction vessels and processes including batch, semi-batch, and continuous processes. As appreciated by the skilled artisan, reaction conditions vary depending on batch size and vessel type. However, when in possession of the teachings contained herein, such conditions are easily determined.

Cleaning Compositions and Cleaning Composition Additives Comprising Applicants' Organic Activators The cleaning composition of the present invention may be advantageously employed for example, in laundry applications, hard surface cleaning, automatic dishwashing applications, as well as cosmetic applications such as dentures, teeth, hair and skin. However, due to the unique advantages of both increased effectiveness in lower temperature solutions and the superior color-safety profile, the organic activators of the present invention are ideally suited for laundry applications such as the bleaching of fabrics through the use of bleach containing detergents or laundry bleach additives. Furthermore, the organic activators of the present invention may be employed in both granular and liquid compositions for use in aqueous cleaning applications as well as cleaning compositions that comprise nonaqueous lipophilic solvents such as dry cleaning compositions. A preferred group of nonaqueous lipophilic fluids include low-volatility nonfluorinated organics, silicones, especially those other than amino functional silicones, and mixtures thereof. Suitable silicones for use as a major component, e.g., more than 50%, of the composition include cyclopentasiloxanes, sometimes termed "D5", and/or linear analogs having approximately similar volatility, optionally complemented by other compatible silicones. Suitable silicones are well known in the literature, see, for example, Kirk Othmer's Encyclopedia of Chemical Technology, and are available from a number of commercial sources, including General Electric, Toshiba Silicone, Bayer, and Dow Corning. Other suitable lipophilic fluids are commercially available from Procter & Gamble or from Dow Chemical and other suppliers. For example, one suitable silicone is SF-1528 available from GE silicone fluids.

The organic activators of the present invention may also be employed in a cleaning additive product. A cleaning additive product including the organic activators of the present invention is ideally suited for inclusion in a wash process when additional bleaching effectiveness is desired. Such instances may include, but are not limited to, low temperature solution cleaning applications. The additive product may be, in its simplest form, Applicants' organic activator. Preferably, the additive could be packaged in dosage form for addition to a cleaning process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of such composition. Suitable filler or carrier materials include, but are not limited to, various salts of sulfate, carbonate and silicate as well as talc, clay and the like. Filler or carrier materials for liquid compositions may be water or low molecular weight primary and secondary alcohols including polyols and diols. Examples of such alcohols include, but are not limited to, methanol, ethanol, propanol and isopropanol. Monohydric alcohols may also be employed. The compositions may contain from about 5% to about 90% of such materials. Acidic fillers can be used to reduce pH. Alternatively, the cleaning additive may include an activated peroxygen source defined below or the adjunct ingredients as fully defined below.

Applicants, cleaning compositions and cleaning additives require an effective amount of Applicants' organic activator. The required level of such activator may be achieved by the addition of one or more embodiments of Applicants' organic activator. As a practical matter, and not by way of limitation, the compositions and cleaning processes herein can be adjusted to provide on the order of at least 1 ppm of Applicants' organic activator in the washing medium, and will preferably provide from about 1 ppm to about 1500 ppm, more preferably from about 5 ppm to about 1000 ppm, and most preferably from about 10 ppm to about 500 ppm of the organic activator in the wash liquor. In order to obtain such levels of Applicants' organic activator in the wash liquor, typical compositions herein will comprise at least 0.1%, preferably from about 0.5% to about 60%, more preferably from about 0.5% to about 40% by weight of the bleaching composition.

In addition to Applicants' organic activators, cleaning compositions must comprise a peroxygen source. Suitable ratios of moles of Applicants' organic activator to moles of peroxygen source include but are not limited to from about 1:1 to about 1:100. Suitable peroxygen sources include, but are not limited to, preformed peracids, a hydrogen peroxide source in combination with another bleach activator, or a mixture thereof. Suitable preformed peracids include, but are not limited to, compounds selected from the group consisting of percarboxylic acids and salts, percarbonic acids and salts, perimidic acids and salts, peroxymonosulfuric acids and salts, and mixtures thereof. Suitable sources of hydrogen peroxide include, but are not limited to, compounds selected from the group consisting of perborate compounds, percarbonate compounds, perphosphate compounds and mixtures thereof.

Suitable bleach activators that may be used in conjunction with Applicants' organic activator include, but are not limited to, tetraacetyl ethylene diamine (TAED), benzoylcaprolactam (BzCL), 4-nitrobenzoylcaprolactam, 3-chlorobenzoylcaprolactam, benzoyloxybenzenesulphonate (BOBS), nonanoyloxybenzenesulphonate (NOBS), phenyl benzoate (PhBz), decanoyloxybenzenesulphonate ($C_{10}$-OBS), benzoylvalerolactam (BZVL), octanoyloxybenzenesulphonate ($C_8$-OBS), perhydrolyzable esters, perhydrolyzable carbonates, perhydrolyzable imides and mixtures thereof.

When present, hydrogen peroxide sources will typically be at levels of from about 1%, preferably from about 5% to about 30%, preferably to about 20% by weight of the cleaning composition. If present, peracids or bleach activators will typically comprise from about 0.1%, preferably from about 0.5% to about 60%, more preferably from about 0.5% to about 40% by weight of the cleaning composition.

In addition to the disclosure above, suitable types and levels of peroxygen and activated peroxygen sources are found in U.S. Pat. Nos. 5,576,282, 6,306,812 B1 and 6,326,348 B1 that are incorporated by reference.

The cleaning compositions herein will preferably be formulated such that, during use in aqueous cleaning operations, the wash water will have a pH of between about 6.5 and about 11, preferably between about 7.5 and about 10.5. Liquid dishwashing product formulations preferably have a pH between about 6.8 and about 9.0. Laundry product formulations typically have a pH of from about 9 to about 11. Techniques for controlling pH at recommended usage levels include the use of buffers, alkalis, acids, etc., and are well known to those skilled in the art.

Adjunct Materials

While not essential for the purposes of the present invention, the non-limiting list of adjuncts illustrated hereinafter are suitable for use in the instant cleaning compositions and may be desirably incorporated in preferred embodiments of the invention, for example to assist or enhance cleaning performance, for treatment of the substrate to be cleaned, or to modify the aesthetics of the cleaning composition as is the case with perfumes, colorants, dyes or the like. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306, 812 B1 and 6,326,348 B1.

Surfactants—Preferably, the cleaning compositions of the present invention comprise a surfactant or surfactant system wherein the surfactant can be selected from nonionic and/or anionic and/or cationic surfactants and/or ampholytic and/or zwitterionic and/or semi-polar nonionic surfactants.

The surfactant or surfactant system is typically present at a level of from about 0.1%, preferably from about 1%, more preferably from about 5% by weight of the cleaning compositions to about 99.9%, preferably about 80%, more preferably about 35%, most preferably about 30% by weight of the cleaning composition.

Builders—The cleaning compositions of the present invention preferably comprise one or more detergent builders or builder systems. When present, the compositions will typically comprise at least about 1% builder, preferably at least about 5%, more preferably from about 10% to about 80%, preferably to about 50%, more preferably to about 30% by weight of the cleaning composition.

Builders include, but are not limited to, the alkali metal, ammonium and alkanolammonium salts of polyphosphates, alkali metal silicates, alkaline earth and alkali metal carbonates, aluminosilicate builders polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The cleaning compositions of the present invention may also optionally contain one or more copper, iron and/or manganese chelating agents.

If utilized, chelating agents will generally comprise from about 0.1%, more preferably from about 3.0% to about 15% by weight of the cleaning composition.

Dye Transfer Inhibiting Agents—The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

When present in the cleaning compositions of the present invention, the dye transfer inhibiting agents are present at levels from about 0.0001%, more preferably from about 0.01%, most preferably from about 0.05% by weight of the cleaning compositions to about 10%, more preferably about 2%, most preferably about 1% by weight of the cleaning composition.

Dispersants—The cleaning compositions of the present invention can also contain dispersants. Suitable water-soluble organic salts are the homo- or co-polymeric acids or their salts, in which the polycarboxylic acid comprises at least two carboxyl radicals separated from each other by not more than two carbon atoms.

Enzymes—The cleaning compositions can comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and known amylases, or mixtures thereof. A preferred combination is a cleaning composition having a cocktail of conventional applicable enzymes like protease, lipase, cutinase and/or cellulase in conjunction with the amylase of the present invention.

Enzyme Stabilizers—Enzymes for use in detergents can be stabilized by various techniques including the use of water-soluble sources of calcium and/or magnesium ions in the finished cleaning compositions.

Catalytic Metal Complexes—Applicants' cleaning compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243 Bragg, issued Feb. 2, 1982.

If desired, the compositions herein can be catalyzed by means of a manganese compound. Such compounds and levels of use are well known in the art and include, for example, the manganese-based catalysts disclosed in U.S. Pat. No. 5,576,282 Miracle et al.

Cobalt bleach catalysts useful herein are known, and are described, for example, in U.S. Pat. No. 5,597,936 Perkins et al., issued Jan. 28, 1997; U.S. Pat. No. 5,595,967 Miracle et al., Jan. 21, 1997. The most preferred cobalt catalyst useful herein are cobalt pentaamine acetate salts having the formula $[Co(NH_3)_5OAc]T_y$, wherein "OAc" represents an acetate moiety and "$T_y$" is an anion, and especially cobalt pentaamine acetate chloride, $[Co(NH_3)_5OAc]Cl_2$. Such cobalt catalysts are readily prepared by known procedures, such as taught for example in U.S. Pat. No. 5,597,936, and U.S. Pat. No. 5,595,967.

Compositions herein may also include a transition metal complex of a macropolycyclic rigid ligand—abreviated as "MRL". As a practical matter, and not by way of limitation, the compositions and cleaning processes herein can be adjusted to provide on the order of at least one part per hundred million of the active MRL species in the aqueous washing medium, and will preferably provide from about 0.005 ppm to about 25 ppm, more preferably from about 0.05 ppm to about 10 ppm, and most preferably from about 0.1 ppm to about 5 ppm, of the MRL in the wash liquor.

Suitable metals in the MRLs include Mn(II), Mn(III), Mn(IV), Mn(V), Fe(II), Fe(III), Fe(IV), Co(I), Co(I), Co(II), Ni(I), Ni(II), Ni(EII), Cu(I), Cu(II), Cu(III), Cr(II), Cr(III), Cr(IV), Cr(V), Cr(VI), V(VII), V(IV), V(V), Mo(IV), Mo(V), Mo(VI), W(IV), W(V), W(VI), Pd(II), Ru(II), Ru(III), and Ru(IV). Preferred transition-metals in the instant transition-metal bleach catalyst include manganese, iron and chromium.

Suitable MRL's herein comprise:
 (a) at least one macrocycle main ring comprising four or more heteroatoms; and
 (b) a covalently connected non-metal superstructure capable of increasing the rigidity of the macrocycle, preferably selected from
   (i) a bridging superstructure, such as a linking moiety;
   (ii) a cross-bridging superstructure, such as a cross-bridging linking moiety; and
   (iii) combinations thereof.

Suitable transition metal MRLs are readily prepared by known procedures, such as taught for example in WO 00/32601, and U.S. Pat. No. 6,225,464.

Processes of Making and Using of Applicants' Cleaning Composition

The cleaning compositions of the present invention can be formulated into any suitable form and prepared by any process chosen by the formulator, non-limiting examples of which are described in U.S. Pat. No. 5,879,584 Bianchetti et al., issued Mar. 9, 1999; U.S. Pat. No. 5,691,297 Nassano et al., issued Nov. 11, 1997; U.S. Pat. No. 5,574,005 Welch et al., issued Nov. 12, 1996; U.S. Pat. No. 5,569,645 Dinniwell et al., issued Oct. 29, 1996; U.S. Pat. No. 5,565,422 Del Greco et al., issued Oct. 15, 1996; U.S. Pat. No. 5,516,448 Capeci et al., issued May 14, 1996; U.S. Pat. No. 5,489,392 Capeci et al., issued Feb. 6, 1996; U.S. Pat. No. 5,486,303 Capeci et al., issued Jan. 23, 1996.

Method of Use

The present invention includes a method for cleaning a situs inter alia a surface or fabric. Such method includes the steps of contacting at least a portion of a surface or fabric with an embodiment of Applicants' cleaning composition, in neat form or diluted in a wash liquor, and optionally rinsing such surface or fabric. Preferably the surface or fabric is subjected to a washing step prior to the aforementioned rinsing step. For purposes of the present invention, washing includes but is not limited to, scrubbing, and mechanical agitation. As will be appreciated by one skilled in the art, the cleaning compositions of the present invention are ideally suited for use in laundry applications. Accordingly, the present invention includes a method for laundering a fabric. The method comprises the steps of contacting a fabric to be laundered with a laundry solution comprising at least one embodiment of Applicants cleaning composition, cleaning additive or mixture thereof. The fabric may comprise most any fabric capable of being laundered. Such laundry solution may have a pH of from about 8 to about 10. The cleaning compositions are preferably employed at concentrations of from about 500 ppm to about 10,000 ppm in solution. The water temperatures preferably range from about 5° C. to about 60° C. The water to fabric ratio is preferably from about 1:1 to about 30:1.

EXAMPLE I

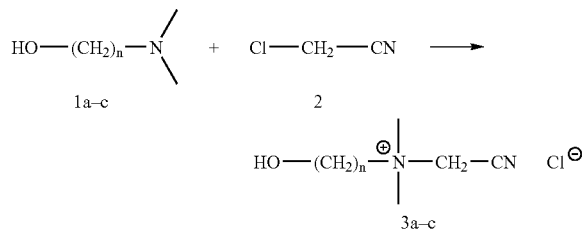

Preparation of 1-cyano-N,N-dimethyl-N-(2-hydroxyethyl)methanaminium chloride (3a, n=2). In a 250 mL round bottomed flask equipped with a magnetic stir bar and pressure-equalizing addition funnel, 10 mmol of 2-(dimethylamino)ethanol (1a, n=2, available from Pfaltz & Bauer, Inc., Waterbury, Conn., 06708) is dissolved in 50 mL anhydrous tetrahydrofuran. The mixture is cooled with an ice bath and 10 mmol chloroacetonitrile (2, available from Fisher Scientific USA, Pittsburgh, Pa., 15275-1126) is added slowly with stirring under an argon atmosphere. Once the addition is complete, the ice bath is removed and the reaction is warmed to room temperature and stirred for 16 hours. The solvent is removed under reduced pressure to obtain 3a.

EXAMPLE II

Preparation of 1-cyano-N,N-dimethyl-N-(3-hydroxypropyl)methanaminium chloride (3b, n=3). The compound 3b is prepared according to the procedure of Example I, substituting 3-(dimethylamino)-1-propanol (1b, n=3, available from Pfaltz & Bauer, Inc., Waterbury, Conn., 06708) in place of 1a.

EXAMPLE III

Preparation of 1-cyano-N,N-dimethyl-N-(6-hydroxyhexyl)methanaminium chloride (3c, n=6). The compound 3c is prepared according to the procedure of Example I, substituting 6-(dimethylamino)-1-hexanol (1c, n=6, available from Pfaltz & Bauer, Inc., Waterbury, Conn., 06708) in place of 1a.

EXAMPLE IV

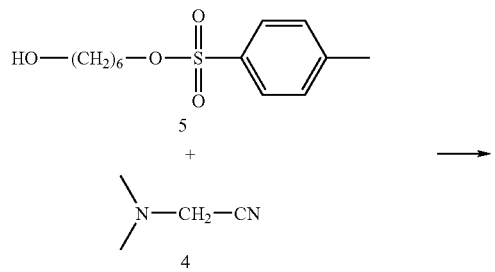

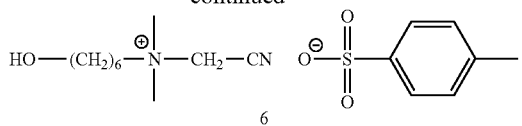

Preparation of 1-cyano-N,N-dimethyl-N-(6-hydroxyhexyl)methanarninium 4-methylbenzenesulfonate (6). In a 250 mL round bottomed flask equipped with a magnetic stir bar and pressure-equalizing addition funnel, 10 mmol of dimethylaminoacetonitrile (4; available from Alfa Aesar, Ward Hill, Mass., 01835-8099) is dissolved in 100 mL tetrahydrofuran. The mixture is cooled with an ice bath and 10 mmol 1,6-hexanediol, mono(4-methylbenzenesulfonate) (5, available from Aldrich Chemical Company, Inc., Milwaukee, Wis., 53233) is added slowly with stirring under an argon atmosphere. Once the addition is complete, the ice bath is removed and the reaction is warmed to room temperature and stirred for 16 hours. The solvent is then removed under reduced pressure to obtain 6.

EXAMPLE V

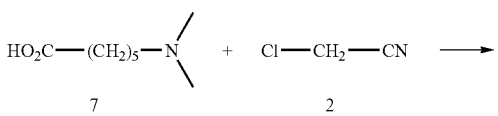

Preparation of 5-carboxy-N,N-dimethyl-N-(cyanomethyl)-1-pentanaminium, inner salt (8). The compound is prepared according to Example I, substituting 6-(Dimethylamino)hexanoic acid (7, prepared as described in Haeggberg, et al. U.S. Pat. No. 5,599,781) in place of 1a.

EXAMPLE VI

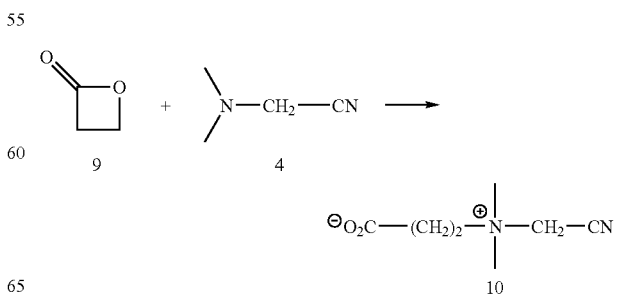

Preparation of 2-carboxy-N,N-dimethyl-N-(cyanomethyl)-1-ethanaminium, inner salt (10). In a 1 L round bottomed flask cooled with an ice bath and equipped with a magnetic stir bar and pressure equalizing addition funnel 0.2 mole of dimethylaminoacetonitrile (4; available from Alfa Aesar, Ward Hill, Mass., 01835-8099) is dissolved in a solution of 250 mL diethyl ether and 75 mL acetonitrile. Next, 0.2 mole 2-oxetanone (9, available from Alfa Aesar, Ward Hill, Mass., 01835-8099) is added slowly under an argon atmosphere to the solution in said 1 L flask. Once the addition is complete, the ice bath is removed and the reaction is warmed to room temperature and stirred for 16 hours. The solvent is then removed under reduced pressure to obtain 10.

EXAMPLE VII

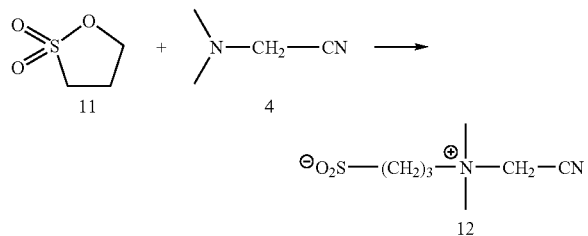

Preparation of N,N-dimethyl-N-(cyanomethyl)-4-sulfo-1-butanaminium, inner salt (12). In a 250 mL round bottomed flask equipped with a magnetic stir bar, reflux condenser, and pressure-equalizing addition funnel, 10 mmol of dimethylaminoacetonitrile (4; available from Alfa Aesar, Ward Hill, Mass., 01835-8099) is dissolved in 50 mL acetonitrile. The mixture is cooled with an ice bath and 10 mmol 1,2-oxathiolane-2,2-dioxide (11, available from Raschig Corporation, Richmond, Va., 23231) is added slowly with stirring under an argon atmosphere. Once the addition is complete, the ice bath is removed and the reaction is warmed to reflux, and stirred for 16 hours, then cooled to room temperature. The solvent is removed under reduced pressure to obtain 12.

EXAMPLE VIII

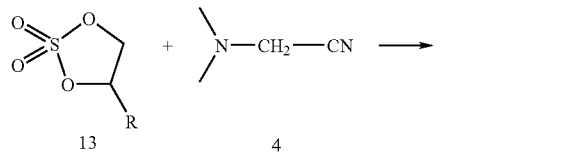

-continued

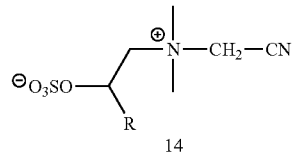

Preparation of N,N-dimethyl-N-(cyanomethyl)-2-(sulfooxy)-1-decanaminium, inner salt (14, R=n-$C_8H_{17}$). The title compound is prepared according to Example VII, substituting 4-octyl-1,3,2-dioxathiolane-2,2-dioxide (13, R=n-$C_8H_{17}$, prepared according to Miracle, et. al., U.S. Pat. No. 5,817,614) for 11.

EXAMPLE IX

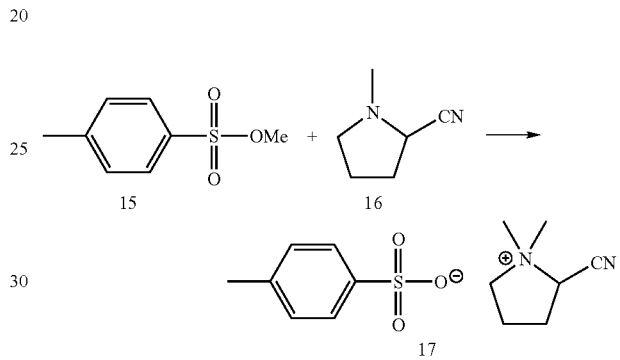

Preparation of 2-cyano-1,1-dimethylpyrrolidinium p-toluenesulfonate (17). In a 250 mL round bottomed flask equipped with a magnetic stir bar, reflux condenser, and pressure-equalizing addition funnel, 10 mmol of 1-methyl-2-pyrrolidinecarbonitrile (16, prepared according to Chiba, et. al., J. Org. Chem. 1977, Vol. 42, No. 18, pp. 2973–7) is dissolved in 50 mL acetonitrile. The mixture is cooled with an ice bath and 10 mmol methyl p-toluenesulfonate (15, available from Aldrich Chemical Company, Inc., Milwaukee, Wis., 53233) is added slowly with stirring under an argon atmosphere. Once the addition is complete, the ice bath is removed and the reaction is warmed to reflux, stirred 16 h, then cooled to room temperature. The solvent is then removed under reduced pressure to obtain 17.

EXAMPLE X

Bleaching detergent compositions having the form of granular laundry detergents are exemplified by the following formulations.

|  | A | B | C | D | E | F |
|---|---|---|---|---|---|---|
| Linear alkylbenzenesulfonate | 20 | 22 | 20 | 15 | 20 | 20 |
| $C_{12}$ Dimethylhydroxyethyl ammonium chloride | 0.7 | 1 | 1 | 0.6 | 0.0 | 0.7 |
| AE3S | 0.9 | 0.0 | 0.9 | 0.0 | 0.0 | 0.9 |
| AE7 | 0.0 | 0.5 | 0.0 | 1 | 3 | 1 |
| sodium tripolyphosphate | 23 | 30 | 23 | 17 | 12 | 23 |

-continued

|  | A | B | C | D | E | F |
| --- | --- | --- | --- | --- | --- | --- |
| Zeolite A | 0.0 | 0.0 | 0.0 | 0.0 | 10 | 0.0 |
| 1.6R Silicate | 7 | 7 | 7 | 7 | 7 | 7 |
| Sodium Carbonate | 15 | 14 | 15 | 18 | 15 | 15 |
| Polyacrylate MW 4500 | 1 | 0.0 | 1 | 1 | 1.5 | 1 |
| Carboxy Methyl Cellulose | 1 | 1 | 1 | 1 | 1 | 1 |
| Savinase 32.89 mg/g | 0.1 | 0.07 | 0.1 | 0.1 | 0.1 | 0.1 |
| Natalase 8.65 mg/g | 0.1 | 0.1 | 0.1 | 0.0 | 0.1 | 0.1 |
| Brightener 15 | 0.06 | 0.0 | 0.06 | 0.18 | 0.06 | 0.06 |
| Brightener 49 | 0.1 | 0.06 | 0.1 | 0.0 | 0.1 | 0.1 |
| Diethylenetriamine pentacetic acid | 0.6 | 0.3 | 0.6 | 0.25 | 0.6 | 0.6 |
| $MgSO_4$ | 1 | 1 | 1 | 0.5 | 1 | 1 |
| Sodium Percarbonate | 0.0 | 5.2 | 0.0 | 0.0 | 0.0 | 0.0 |
| Photobleach | 0.0030 | 0.0015 | 0.0015 | 0.0020 | 0.0045 | 0.0010 |
| Sodium Perborate Monohydrate | 4.4 | 0.0 | 3.85 | 2.09 | 0.78 | 3.63 |
| NOBS | 1.9 | 1.9 | 1.66 | 1.77 | 0 | 0 |
| TAED | 0.38 | 0 | 0.2 | 0.0 | 0 | 0.28 |
| Organic Activator* | 0.2 | 0.58 | 0.15 | 0.5 | 0.3 | 0.3 |
| Sulfate/Moisture | Balance to 100% | Balance to 100% | Balance to 100% | Balance to 100% | Balance to 100% | Balance to 100% |

*Organic activator prepared according to any one of Examples 1 to 9.
Any of the above compositions is used to launder fabrics at a concentration of 1000 ppm to 2500 ppm in water, 20–40° C., and a 15:1 to 20:1 water:cloth ratio. The typical pH is about 9.5 to 10 but can be adjusted by altering the proportion of acid to Na— salt form of alkylbenzenesulfonate.

EXAMPLE XI

A laundry bar suitable for hand-washing soiled fabrics is prepared by a standard extrusion process and comprises the following:

| Component | Weight % |
| --- | --- |
| Organic Activator* | 0.7 |
| TAED | 1.0 |
| NOBS | 0.2 |
| Sodium Perborate Tetrahydrate | 12 |
| $C_{12}$ linear alkyl benzene sulfonate | 30 |
| Phosphate (as sodium tripolyphosphate) | 10 |
| Sodium carbonate | 5 |
| Sodium pyrophosphate | 7 |
| Coconut monoethanolamide | 2 |
| Zeolite A (0.1–10 micron) | 5 |
| Carboxymethylcellulose | 0.2 |
| Polyacrylate (m.w. 1400) | 0.2 |
| Brightener, perfume | 0.2 |
| Protease | 0.3 |
| $CaSO_4$ | 1 |
| $MgSO_4$ | 1 |
| Water | 4 |
| Filler** | Balance to 100% |

*Organic activator prepared according to any one of Examples 1 to 9.
**Can be selected from convenient materials such as $CaCO_3$, talc, clay, silicates, and the like. Acidic fillers can be used to reduce pH.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleaning composition comprising compound having the formula:

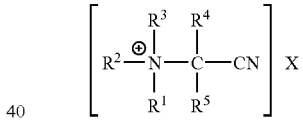

wherein
 a.) $R^1$, $R^2$ and $R^3$ are independently selected from the group consisting of substituted or unsubstituted $C_1$ to $C_{20}$ alkyl moieties;
 b.) $R^4$ and $R^5$ are independently selected from the group consisting of hydrogen, or substituted or unsubstituted $C_1$ to $C_{20}$ alkyl moieties, provided $R^4$ and $R^5$ are not both hydrogen;
 c.) at least one of $R^1$, $R^2$ or $R^3$ is joined with at least one of $R^4$ and $R^5$ to form a ring comprising at least 5 atoms, one of said atoms being the quaternary nitrogen of said compound; and
 d.) X is a charge-equalizing anion, and an adjunct material selected from the group consisting of surfactants, builders, chelating agents, dye transfer inhibiting agents, dispersants, enzymes, enzyme stabilizers, catalytic metal complexes, slay and soil removal/anti-redeposition agents, brighteners, suds suppressors, dyes, perfumes, structure elasticizing agents, fabric softeners, hydrotropes, pigments, and mixtures thereof.

2. A cleaning composition according to claim 1 wherein for said compound only one of $R^1$, $R^2$, or $R^3$ is joined with only one of $R^4$ or $R^5$ to form a ring comprising at least 5 atoms, one of said atoms being the quaternary nitrogen of said compound.

3. A process of making a cleaning composition comprising making compound having the formula:

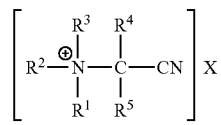

wherein $R^1$, $R^2$ and $R^3$ are independently selected from the group consisting of substituted or unsubstituted $C_1$ to $C_{20}$ alkyl moieties; $R^4$ and $R^5$ are independently selected from the group consisting of hydrogen, or substituted or unsubstituted $C_1$ to $C_{20}$ alkyl moieties, provided that $R^4$ and $R^5$ are not both hydrogen; at least one of $R^1$, $R^2$ or $R^3$ is joined with at least one of $R^4$ and $R^5$ to form a ring comprising at least 5 atoms, one of said atoms being the quaternary nitrogen of said compound; and X, when present, is a charge-equalizing anion, said process comprising the steps of reacting an amine having the formula:

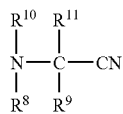

wherein $R^8$, $R^9$, $R^{10}$ and $R^{11}$ are independently selected from the group consisting of substituted or unsubstituted $C_1$ to $C_{20}$ alkyl moieties; and at least one of $R^8$ or $R^{10}$ is joined with at least one of $R^9$ or $R^{11}$ to form a ring comprising at least 5 atoms, one of said atoms being the nitrogen of said amine; with a compound selected from the group consisting of:

$$R^2—Y$$

wherein $R^2$ is as defined above and Y is moiety that upon displacement by the amine becomes X as defined above; or

wherein $R^6$ is $C_1$ to $C_{20}$ substituted or unsubstituted alkylene and G is selected from the group consisting of $OSO_2$, $OSO_3$, $OPO_2$, $OCO_2$, $SO_2$, $SO_3$ and $CO_2$, and combining said compound with an adjunct material selected from the group consisting of surfactants, builders, chelating agents, dye transfer inhibiting agents, dispersants, enzymes, enzyme stabilizers, catalytic metal complexes, slay and soil removal/anti-redeposition agents, brighteners, suds suppressors, dyes, perfumes, structure elasticizing agents, fabric softeners, hydrotropes, pigments, and mixtures thereof.

4. A cleaning composition further comprising a lipophilic fluid according to claim 1.

5. A cleaning composition according to claim 2 further comprising a lipophilic fluid.

6. A method of cleaning a substrate comprising contacting said substrate with a cleaning composition according to claim 1 said method including the optional steps of washing, rinsing, or washing and then rinsing said substrate.

7. A method of cleaning a substrate comprising contacting said substrate with a cleaning composition according to claim 2, said method including the optional steps of washing, rinsing, or washing and then rinsing said substrate.

* * * * *